United States Patent

Ramey et al.

[11] 4,051,102
[45] Sept. 27, 1977

[54] BICYCLIC HINDERED AMINO ACIDS, METAL SALTS THEREOF AND STABILIZED COMPOSITIONS

[75] Inventors: Chester E. Ramey, Spring Valley; John J. Luzzi, Carmel, both of N.Y.

[73] Assignee: Ciba-Geigy Corporation, Ardsley, N.Y.

[21] Appl. No.: 545,259

[22] Filed: Jan. 29, 1975

Related U.S. Application Data

[62] Division of Ser. No. 429,236, Dec. 28, 1973, Pat. No. 3,879,396.

[51] Int. Cl.² .................. C07D 221/22; C08K 5/34; C09K 15/30
[52] U.S. Cl. .................. 260/45.8 N; 252/403; 260/45.7 P; 260/45.75; 260/45.75 K; 260/45.75 N; 260/45.75 R; 260/45.8 NT; 260/45.85 B; 260/45.85 D; 260/45.85 S; 260/45.95 G; 260/270 R; 260/293.54
[58] Field of Search .................. 260/45.8 N, 79.5 B, 260/80.78; 252/403

[56] References Cited

U.S. PATENT DOCUMENTS

| 3,093,620 | 6/1963 | Karcher | 260/79.5 B |
| 3,467,633 | 9/1969 | Harris | 260/80.78 |
| 3,531,447 | 9/1970 | Gumbolt | 260/80.78 |

*Primary Examiner*—H.S. Cockeram
*Attorney, Agent, or Firm*—Nestor W. Shust; Charles W. Vanecek

[57] ABSTRACT

Compounds having the formula

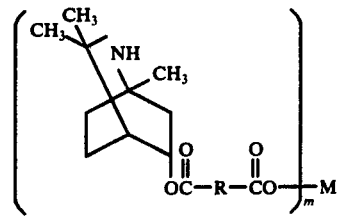

wherein
R is alkylene,
M is hydrogen or a metal, and
m has a value of from 1 to 4, are good light stabilizers. The amino acids may be formed, for example, from 1,3,3-trimethyl-3-azabicyclo[2.2.2]octane-5-ol and sebacic acid to given o-mono(1,3,3-trimethyl-2-azabicyclo[2.2.2]octane-5-ol)sebacate. The metal salts of the acids are readily prepared by reacting the acids or their salts with a reactive form of the metal or metal complex.

14 Claims, No Drawings

BICYCLIC HINDERED AMINO ACIDS, METAL SALTS THEREOF AND STABILIZED COMPOSITIONS

This is a divisional of application Ser. No. 429,236 filed on Dec. 28, 1973, now U.S. Pat. No. 3,879,396.

BACKGROUND OF THE INVENTION

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It has been proposed to stabilize polymeric materials against ultraviolet light deterioration by the use of various types of ultraviolet absorbers, Thus, U.S. Pat. No. 3,004,896 discloses for this purpose 2(2-hydroxyphenyl)benzotriazole derivatives, while U.S. Pat. No. 3,189,630 discloses certain metal salts of hydroxybenzoic acids which are useful as actinic stabilizers in synthetic polymers.

DETAILED DISCLOSURE

The present invention is directed to a class of ultraviolet light stabilizers which consist of a compound of the formula

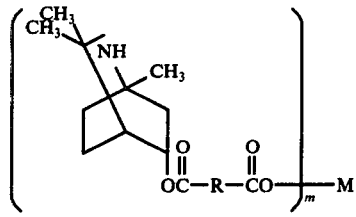

I wherein

R is straight- or branched-chain alkylene having 1 to 20 carbon atoms,

M is hydrogen or a metal selected from the group consisting of barium, nickel, manganese, calcium, zinc, iron, sodium, cobalt tin, and dialkyl tin, and $m$ has a value of from 1 to 4, the value of $m$ being the same as the available valence of M.

In a preferred embodiment of the compound of formula I, R is straight-chain alkylene having 1 to 8 carbon atoms; more preferably, when R is straight-chain alkylene having 1 to 8 carbon atoms, $m$ has a value of 1 or 2, with the most preferred substituents represented by M being hydrogen, nickel and manganese.

This invention also relates to compositions of matter which are stabilized against ultraviolet light deterioration which comprises a synthetic organic polymer normally subject to ultraviolet deterioration containing from about 0.005 to 5% by weight of the polymer of the compounds of formula I and preferably from 0.01 to 2% by weight.

The substituted piperazinedione carboxylic acids and metal salts thereof, as represented by formula I, can be used in combination with other light stabilizers such as 2(2-hydroxyphenyl)benzotriazoles, 2-hydroxybenzopheones, nickel complexes and benzoates. The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, cross-linked polyethylene, polypropylene, poly(4-methylpentane-1 and the like, including copolymers of $\alpha$-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene; polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly (3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and the other chemicals used in rubber compounding, plasticizers, color stabilizers, di- and tri-alkyl- and -alkylphenylphosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

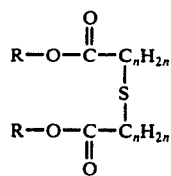

wherein R is an alkyl group having from 6 to 24 carbon atoms; and $n$ is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005 to 5% and preferably from 0.01 to 2% by weight Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Amoung these phenolic antioxidants are included the following:

di-n-octadecyl (3-5-butyl-4-hydroxy-5-methylbenzyl)malonate 2,6-di-t-butylphenol 2,2'-methylene-bis(6-t-butyl-4-methylphenol)

2,6-di-t-butylhydroquinone octadecyl-(3,5-di-t-butyl-4-hydroxybenzylthio)acetate 1,1,3-tris(3-t-butyl-6-methyl-4-hydroxyphenyl)butane 1,4-bis(3,5-di-t-butyl-4-hydroxybenzyl)-2,3-5,6tetramethylbenzene 2,4-bis-(3,5-di-t-butyl-4-hydroxyphenoxy)-6-(n-octylthio)-1,3,5-triazine 2,4-bis-(4-hydroxy-3,5-di-t-butylphenoxy)-6-(n-octylthioethylthio)-1,3,5-triazine 2,4-bis-(n-octylthio)-6-(3,5-di-t-butyl-4-hydroxyanilino)-1,3,5-triazine 2,4,6-tris-(4-hydroxy-3,5-di-t-butylphenoxy)-1,3,5-triazine n-octadecyl-β-(3,5-di-t-butyl-4-hydroxyphenyl)propionate n-octadecyl-3,5-di-t-butyl-4-hydroxybenzoate 2-(n-octylthio)ethyl-3,5-di-t-butyl-4-hydroxybenzoate stearamido N,N-bis-{ethylene 3-(3,5-di-t-butyl-4-hydroxyphenyl)propionate}

1,2-propylene glycol bis-{3(3,5-di-t-butyl-4-hydroxyphenyl)propionate} pentaerythritol tetrakis-{3-(3,5-di-t-butyl-4-hydroxyphenyl)propionate} dioctadecyl-3,5-di-t-butyl-4-hydroxybenzylphosphonate di-n-octadecyl-1-(3,5-di-t-butyl-4-hydroxyphenyl)-ethanephosphonate The above phenolic hydrocarbon stabilizers are known and many are commercially available.

The above antioxidants have been listed only for the purpose of illustration and it is important to note that any other antioxidant can be employed with similar improved results. The above exemplified anti-oxidants and other related antioxidants which are incorporated, herein by reference, are disclosed in greater detail in the following patents: Netherlands Pat. No. 67/1119, issued Feb. 19, 1968; Netherlands Pat. No. 68/03498 issued Sept. 18, 1968; U.S. Pat. Nos. 3,255,191; 3,330,859, 3,644,482, 3,281,505; 3,531,483, 3,285,855; 3,364,250; 3,368,997; 3,357,944 and 3,758,549.

The bicyclic hindered amino acids of formula I may be prepared by reacting a compound of the formula

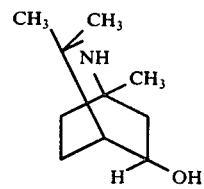

via a usual esterification procedure with a diacid of the formula

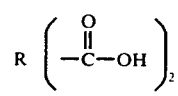

wherein R is as defined above, or conveniently with an acid anhydride thereof in the case of succinic anhydride, glutaric anhydride and the like. In the process of reacting an acid of formula III with a compound of formula II the esterification catalyst is preferably a neutral catalyst, for instance a tetraalkyl titanate.

The acids and acid anhhdrides which are reacted with the compounds of formula II may all be prepared by methods well known in the art.

The metal salts of the present invention per se can be prepared by treating the bicyclic hindered amino acids of formula I with a reactive form of the metal or metal complex, e.g., sodium hydroxide or the like. Alternatively, and preferably in the case of metal complexes and metals other than the alkali metals, a double decomposition is employed. Thus, for example, a sodium salt of the present invention is treated with nickel chloride. In a similar fashion use of other halides such as manganese dichloride, barium chloride and the like results in formation of the corresponding metal derivative.

The compounds of formula II may be prepared according to the procedure described in British Pat. No. 1,231,380 and in A. Rassat and P. Rey, Tetrahedron 28, 741 (1972).

Synthesis of the intermediate piperitenone, of the formula

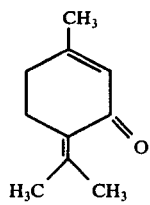

which is used in the preparation of the above-mentioned compound of formula II, as described in the above two references, is described in J.J. Beereboom, J. Org. Chem. 31, 2026 (1966). Piperitenone has also been isolated as a natural product from essential oils, as reported in Y. R. Naves, Helv. Chem. Acta, 24. 722 (1951) and S. Schimizer, N. Skeda, and H. Udea, Bull. Arg. Chem. Soc. Japan, 24, 324 (1960) and obtained by the oxidation of geranic acid, as reported in J. J. Berreboom, J. Am. Chem. Soc., 85, 3525 (1963).

The following examples, presented for illustration and not limitation, will further serve to typify the nature of the present invention.

EXAMPLE 1

Piperitenone

A. To 1.01 of dry tetrahydrofuran contained in a 5-liter 3-necked flask equipped with a stirrer, thermometer, condenser with drying tube, nitrogen inlet and dropping funnel was added 40.0 g (0.73 moles) of pulverized 85% KOH. To the resulting suspension was added, with stirring and cooling with an ice-salt bath, 686 g of mesityl oxide at such a rate as to maintain the temperature of the reaction mixture below 30° C. To the resulting solution was next added a solution of 178 g (2.5 moles) of methyl vinyl ketone in 196 g (total, 9 moles) of mesityl oxide over a period of 0.8 hours while the temperature of the reaction mixture was maintained at 15° to 20° C. The reaction mixture was then allowed to warm to room temperature and heated slowly to gentle boiling under reflux. After maintaining the boiling for 0.5 hours, the reaction mixture was cooled and 43 ml of glacial acetic acid was added with stirring and cooling. The solvent and excess mesityl oxide were removed by distillation under a slight vacuum to a head temperature of 78° C and the residue was distilled under reduced pressure. The fraction boiling at 115° to 133°/9 mm was retained. GLPC (20% silicon gum rubber, one-fourth inch 10 ft. column isothermal at 160° C) of this fraction indicated that the anticipated products (piperitenone and isomers) were present.

To crude distillate (290 g) was added dropwise with stirring to a solution of 560 g of sodium sulfite in 21 of water. The solution was heated to 85° C and 128 ml of glacial acetic acid was added dropwise over a 2 hour period to maintain the pH at 8-9. When the pH became steady for about 0.5 hour., the mixture was cooled to room temperature and extracted with 3 × 250 ml ether. The aqueous layer was cooled in an ice bath and the pH was adjusted to 13 by the addition of 70 ml of 50% NaOH. The basic aqueous solution was then extracted with 4 × 300 ml of ether. The ether extracts were combined dried over anhydrous sodium sulfate and evaporated to give 60.6 g of piperitenone, 96% pure by GLPC.

B. Among other methods of preparation, piperitenone is prepared in an analogous manner to the procedure described in (A) by substituting for the KOH, tetrahydrofuran used therein the following base, solvent combinations:

sodium t-pentoxide, toluene; barium oxide, benzene; potassium t-butoxide, tetrahydrofuran; sodium hydride, tetrahydrofuran.

EXAMPLE 2

1,3,3-Trimethyl-2-azabicyclo[2.2.2] octane 5-one hydrochloride

A. In a 2-liter Morton flask equipped with a condenser, stirrer, thermometer and ice-salt cooling bath was placed 1200 ml of concentrated ammonium hydroxide. To the flask was added dropwise with cooling and stirring 60.0 g (0.40 moles) of piperitenone over a 45 minute period. The reaction mixture was allowed to stir and stand at 0°-5° C for 4 days, then allowed to warm to room temperature and stir overnight. The aqueous solution was then saturated with sodium chloride and extracted 3 × 300 ml with ether. The ether extracts were combined and dried over anhyrous sodium sulfate and evaporated under reduced pressure. The residue (55.5 g) was distilled at 30° to 35°/0.003 mm giving 45.5 g of material of about 85% purity by titration with standard perchloric acid in acetic acid with crystal violet as indicator. A portion of the distillate (38.0 g) was dissolved in 700 ml ether and the ether solution cooled to 5°. With stirring and cooling, anhydrous HCl was bubbled into the ether until precipitation was complete. The ether solution was heated to 50° for 15 minutes, cooled, and filtered. The collected solid was washed well with ether and dried over $P_2O_5$ in a vacuum oven, giving 39.0 g of the desired aminoketone hydrochloride. A small sample of the hydrochloride was recrystallized from isopropanol, giving a white crystalline solid, m.p. 200°-204° C.

B. Among other methods of preparation, the reaction described under (A) above is also performed by substituting anhydrous ammonia for the concentrated ammonium hydroxide, by replacing the aqueous medium with a non-reactive solvent such as an ether, hydrocarbon or alcohol, and by preferably conducting the reaction at greater then atmospheric pressure.

EXAMPLE 3

1,3,3-Trimethyl-3-azabicyclo[2.2] octane-5 ol

A. In a 1-1 3-necked flask equipped with a stirrer, thermometer, condenser and drying tube was placed 26.7 g (0.131 moles) of 1,3,3-trimethyl-2-azabicyclo[2.2.2]octane-5-one hydrochloride and 300 ml of absolute ethanol. The reaction mixture was cooled to 5° C with an ice-salt bath and 131 ml of 1 NKOH in methanol was added dropwise. To the solution was then added in small portions 2.6 g (0.069 moles) of NaBH$_4$ over a 0.5 hour period. The solution was allowed to stir at 0.5° C for 1.5 hours and then allowed to warm to room temperature and stir overnight. The reaction mixture was then made acidic by the addition of 78 ml of concentrated HCl, filtered and the filtrate was evaporated to dryness under reduced pressure. The residue was brought to pH 12 with 2 NKOH and extracted 3 × 100 ml with Ch$_2$Cl$_2$. The organic extracts were combined, dried over anhydrous potassium carbonate and evaporated, yielding 9.5 g of colorless crystals, m.p. 120° to 123° C*, after recrystallization from hexane.

lit., m.p. 123° C (A. Rassat & P. Rey, Tetrahedron 28 741 (1972).

B. Among other methods of preparaton, the reaction described under (A) above is also performed by replacing the reducing medium by:

lithium aluminum hydride/ether or tetrahydrofuran; lithium/liquid NH$_3$/ethanol; lithium/liquid NH$_3$; sodium/ethanol.

The latter two reagents give a mixture of two isomeric alcohols.

EXAMPLE 4

O-mono(1,3,3-trimethyl-2-azabicyclo [2.2.2]octane-5-ol)sebacate

A. In a 500 ml 3-necked flask equipped with a stirrer, thermometer, condenser with water separator and drying tube, and a nitrogen inlet were placed 4.00 g (0.0236 moles) of 1,3,3-trimethyl-2-aza-bicyclo[2.2.2]octane-5-ol, 200 ml of xylene, 5.97 g (0.0295 moles) of sebacic acid and 0.7 ml (0.0295 moles) of tetraisopropyl titanate. The reaction mixture was heated under reflux for a total of 30 hours. At the end of this time, the xylene was decanted from an oily precipitate and the solution evaporated under reduced pressure. The residues were combined, triturated with isopropanol and ether and recrystallized from ethyl acetate, giving colorless crystals, m.p, 132° to 134° C of the desired material.

B. By the following the above procedure (A), and substituting for the sebacic acid an equivalent amount of:
  a. succinic acid
  b. dodecanedicarboxylic acid
  c. tetramethylsuccinic acid
  d. adipic acid
  e. glutaric acid there is respectively obtained the following compounds:
   a. o-mono(1,3,3-trimethyl-2-azabicyclo [2.2.2]octane-5-ol)succinate
   b. o-mono(1,3,3-trimethyl-2-azabicyclo [2.2.2]octane-5-ol)dodecanedicarboxylate
   c. o-mono(1,3,3-trimethyl-2-azabicyclo [2.2.2]octane-5-ol)tetramethylsuccinate
   d. o-mono(1,3,3-trimethyl-2-azabicyclo [2.2.2]octane-5-ol)adipate
   e. o-mono(1,3,3-trimethyl-2-azabicyclo[2.2.2]octane-5-ol)glutarate

EXAMPLE 5

Ni(II) bis{o-mono(1,3,3-trimethyl-2-azabicyclo[2.2.2]octane-5-ol}sebacate

A. In a 500 ml 1-necked flask equipped with a magnetic stirrer, thermometer and dropping funnel were placed 1.41 g (0.004 moles) of o-mono (1,3,3-trimethyl-2-azabicyclo[2.2.2]octane-5-ol) sebacate and 100 ml of absolute methanol. To the stirred suspension was added 4.0 ml of 1.0N KOH in methanol. To the resulting solution was next added dropwise a solution of 0.476 g (0.002 moles) of NiCl$_2$ 6H$_2$O in 50 ml of methanol. The reaction mixture was heated for 2 hours at 50° C and then evaporated under reduced pressure. To the residue was added 200 ml of isopropanol and the mixture was heated for 2 hours at 50° C, then cooled and filtered with suction. The filtrate was evaporated under reduced pressure and the residue dissolved in 200 ml of dry benzene. The benzene solution was filtered with suction and the filtrate evaporated under reduced pressure and dried 2 hours at 50° C giving 1.53 g of the desired material as a green glassy solid.

B. By following the above procedure (A), and substituting for the o-mono(1,3,3-trimethyl-2-azabicyclo[2.2.2]octane-5-ol)sebacate an equivalent amount of
  a. o-mono(1,3,3-trimethyl-2-azabicyclo [2.2.2]octane-5-ol)succinate
  b. o-mono(1,3,3-trimethyl-2-azabicyclo [2.2.2]octane-5-ol)dodecanedicarboxylate
  c. o-mono(1,3,3-trimethyl-2-azabicyclo [2.2.2]octane-5-ol)tetramethylsuccinate
  d. o-mono(1,3,3-trimethyl-2-azabicyclo [2.2.2]octane-5-ol)adipate
  e. o-mono(1,3,3-trimethyl-2-azabicyclo [2.2.2]octane-5-ol)glutarate
there is respectively obtained
  a. nickel complex of bis{o-mono(1,3,3-trimethyl-2-azabicyclo[2.2.2]octane-5-ol)succinate}
  b. nickel complex of bis{o-mono(1,3,3-trimethyl-2-azabicyclo[2.2.2]octane-5-ol)dodecanedicarboxylate}
  c. nickel complex of bis{o-mono(1,3,3-trimethyl-2-azabicyclo[2.2.2.]octane-5-ol)tetramethylsuccinate}
  d. nickel complex of bis{o-mono(1,3,3-trimethyl-2-azabicyclo[2.2.2.]octane-5-ol)adipate}
  e. nickel complex of bis{o-mono(1,3,3-trimethyl-2-azabicyclo[2.2.2]octane-5-ol)glutarate}

EXAMPLE 6

By essentially following the procedure of Example 5(A) and substituting the following metal complexes for nickel chloride:
  a. manganese chloride
  b. zinc chloride
  c. ferric chloride
  d. cobalt(ous) chloride
there is thus respectively obtained:
  a. manganese complex of bis{o-mono(1,3,3-trimethyl-2-azabicyclo[2.2.2]octane-5-ol)sebacate}
  b. zinc complex of bis{o-mono(1,3,3-trimethyl-2-azabicyclo[2.2.2]octane-5-ol)sebacate}
  c. iron complex of bis{o-mono(1,3,3-trimethyl-2-azabicyclo[2.2.2]octane-5-ol)sebacte} d. cobalt comples of bis{o-mono(1,3,3-trimethyl-2-azabicyclo[2.2.2]octane-5-ol)sebacte}.

EXAMPLE 7

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

a. Sample Preparation 5 mil Film — Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sunlamps and black lights (20 of each). The 5 mil sample film which are mounted on 3 × 2 IR card holders with $\frac{1}{4}$ × 1 inch windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results below were obtained according to the procedures described above. The amounts of the additives are expressed in weight percent based on the weight of the polymer.

a. 2-hydroxy-4-methoxy-5-sulfobenzophenone trihydrate
b. 2-hydroxy-4-n-octoxybenzophenone
c. {2,2'-thiobis(4-t-octylphenolate)}-n-butylamine nickel II
d. p-octylphenyl salicylate
e. 2,2'-dihydroxy-4,4'-dimethoxybenzophenone
f. 2(2'-hydroxy-5'-methylphenyl)-benzotriazole.

EXAMPLE 8

High impact polystyrene resin containing elastomer (i.e., butadiene-styrene) is stabilized against loss of elongation properties due to exposure to ultraviolet light by incorporation of 0.3% by weight of o-mono(1,3,3-trimethyl-2-azabicyclo[2.2.2] octane-5-ol)adipate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into a sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portions of the strips are placed in an FS/BL chamber according to Example 7(B) except that the samples are mounted and white cardboard stock and the time to 50% reduction in elongation is measured. The stabilized polystyrene resin retains its elongation property longer than the unstabilized resin.

EXAMPLE 9

Unstabilized linear polyethylene is solvent blended in methylene chloride with 0.5% by weight of the substrate of the nickel complex of o-mono (1,3,3-trimethyl-

TABLE I

| Light Stabilization Data in Polypropylene | | |
|---|---|---|
| | Absorbance Unites | |
| Additive | Formulation A* | Formulation B** |
| o-mono(1,3,3-trimethyl-2-azabicyclo [2.2.2]octane-5-ol)sebacate | 1380 | 1785 |
| Nickel bis[o-mono(1,3,3-trimethyl-2-azabicyclo[2.2.2]octane-5-ol)sebacate] | 2560 | 2400 |
| Control (no additive) | 210 | 755 |

*Formulation A contains 0.5% additive and 0.2% antioxidant dioctadecyl(3,5-di-t-butyl-4-hydroxybenzyl)-phosphonate.
**Formulation 3 contains 0.25% additive, 0.25% U.V. absorber 2-(2'-hydroxy-3',5'-di-t-butylphenyl)-5-chlorobenzotriazole, and 0.2% antioxidant dioctadecyl(3,5-di-t-butyl-4-hydroxybenzyl)phoxphonate.
Proportionately good stabilization is obtained when the compositions of Table 1 the compounds of this invention are present in the concentrations of 0.1% and 1%.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-methylbenzyl)-malonate, 2,4-bis (n-octylthio)-6-(3,4-di-t-butyl-4-hydroxyaniline)-1,3,5-triazine, octadecyl 3-(3',5'-di-t-butyl-4'-hydroxyphenyl)propionate, pentaerythritol-tetra-kis{3,5-di-t-butyl-4-hydroxyphenyl)}propionate, tris-(3,5-di-t-butyl-4-hydroxybenzyl)isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzyl.

The compositions of Table I are also stabilized with 2(2'-hydroxy-3',5'-di-t-butylphenyl)-5-chlorobenzotriazole is replaced with the following UV absorbers:

2-azabicyclo[2.2.2]octane-5-ol) succinate and then vacuum dried. The resin is then extrusion compounded on a 1 inch 24/1=L/D extruder, melt temperature 450° F (232° C) and pressed for 7 minutes at a temperature of 163° C and a pressure of 2000 psi into a sheet of uniform thickness of 100 mil. The sheets are then cut into plaques of 2 inch × 2 inch. The plaques are then exposed in a FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 10

A quantity of SBR emulsion containing 100 g of rubber (500 ml of 20% SBR obtained from Texas U.S., Synpol 1500) previously stored under nitrogen, is placed in a breaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for one-half hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40°–45° C.

The dried rubber (25 g) is heated under nitrogen at 125° C in a Brabender mixer and to this is added with mixing 0.25 g (0.5%) of o-mono(1,3,3-trimethyl-2-azabicyclo[2.2.2]octane-5-ol)glutarate. The composition is mixed for 5 minutes after which it is cooled and compression molded at 125° C into 5° × 0.025 inch plaques.

The plaques are exposed to a xenon arc weatherometer and the color measurement (L-b) is made after 45, 125 and 290 hours. The samples stabilized with the above compound are found to be much more light stable than the unstabilized samples.

EXAMPLE 11

To 50 g of polyacetal resin containing 0.1% of an acid scavenger, dicyandiamide, is added 0.2% by weight of the nickel complex of o-mono(1,3,3-trimethyl-2-azabicyclo[2.2.2]octane-5-ol)sebacate and milled for 7 minutes at 200° C in a Brabender Plasti-recorder. The milled formulation is subsequently pressed into a 40 mil sheet at 215° C at 350 psi for 90 seconds then cooled quickly in a cold press at 350 psi. The stabilized sheets are then remolded for 2 minutes at contact pressure and for 3 minutes at 300 psi at 215° C to give plaques 1½ inch × 2¼ inch × 125 mil. Thereafter, the testing procedure of Example 9 is followed to determine the light stability of the samples. The stabilized samples are found to be much more stable than the unstabilized samples.

EXAMPLE 12

Unstabilized thoroughly dried polyethylene terephthalate chips are dry blended with 1.0% of manganese complex of bis{o-mono(1,3,3-trimethyl-2-azabicyclo[2.2.2]octane-5-ol)sebacate}. 60/10 denier multifilament is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

EXAMPLE 13 a. A composition comprising acrylonitrile-butadiene-styrene terepolymer and 1% by weight of the nickel complex of bis{o-mono(1,3,3-trimethyl2-azabicyclo[2.2.2]octane-5-ol)succinate} resists embrittlement due to exposure to ultraviolet light longer than one which does not contain the stabilizer.

b. A composition comprising polyurethane prepared from toluene diisocyanate and alkylene polyols and 1.0% by weight of nickel complex of bis{o-mono(1,3,3-trimethyl-2-azabicyclo[2.2.2]octane-5-ol)succinate} is more stable to sunlight, fluorescent sunlamps, black lights and fluorescent lights than the unformulated polyurethane.

c. A composition comprising a polycarbonate prepared from bisphenol-A and phosgene and 1% by weight of nickel complex of bis{o-mono(1,3,3-trimethyl-2-azabicyclo[2.2.2]octane-5-ol)succinate} resists discoloration due to exposure to ultraviolet light longer than one which does not contain the stabilizer.

d. A composition comprising polymethylmethacrylate and 0.25% by weight of the nickel complex of bis{o-mono(1,3,3-trimethyl-2-azabicyclo[2.2.2]octane-5-ol)succinate} resists discoloration due to exposure to ultraviolet light longer than one which does not contain the stabilizer.

EXAMPLE 14 a. A stabilized polyamide (nylon 6,6) is prepared by incorporating therein 0.1% of the manganese complex of bis[(1,3,3-trimethyl-2-azabicyclo[2.2.2]octane-5-ol)sebacate]. The light stability of the stabilized composition is superior to that of an unstabilized polyamide.

b. A stabilized polyphenylene oxide polymer (prepared by polymerizing 2,6-dimethylphenol is prepared by incorporating therein 0.5% by weight of the manganese complex of bis{o-mono(1,3,3-trimethyl-2-azabicyclo[2.2.2]octane-5-ol)sebacate}. The stabilized compositions resist embrittlement due to exposure to ultraviolet light longer than one which does not contain the stabilizer.

c. A stabilized crystalline polystyrene is prepared by incorporating therein 0.1% by weight of the zinc complex of bis{o-mono(1,3,3-trimethyl-2-azabicyclo[2.2.2]-octane-5-ol)sebacate}. The stabilized composition resists embrittlement due to exposure to ultraviolet light longer than one which does not contain the stabilizer.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-4-methylbenzyl)malonate, 2,4-bis(n-octylthio)-6-(3,5-di-t-butyl-4-hydroxyaniline)-1,3,5-triazine, octadecyl 3-(3',5'-di-t-butyl-4'-hydroxyphenyl)propionate, pentaethylerythritol-tetrakis[3-(3,5-di-t-butyl-4-hydroxyphenyl)propionate] and tris-(3,5-di-t-butyl-4-hydroxybenzyl)isocyanaurate, respectively.

What is claimed is:

1. A composition of matter stabilized against ultraviolet deterioration which comprises a synthetic organic polymer normally subject to ultraviolet deterioration containing from 0.005 to 5% of a stabilizing compound of the formula

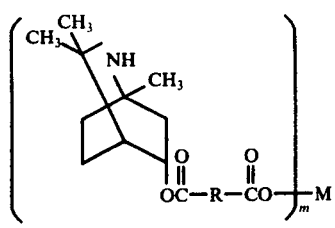

wherein
- R is straight- or branched-chain alkylene having 1 to 20 carbon atoms,
- M is hydrogen or a metal selected from the group consisting of barium, nickel, manganese, calcium, zinc, iron, sodium, cobalt, tin, and dialkyl tin, and
- m has a value of from 1 to 4, the value of m being the same as the available valence of M.

2. A composition according to claim 1 wherein R is straight-chain alkylene having 1 to 8 carbon atoms,
- M is hydrogen or a metal selected from nickel and manganese; and
- m has a value of 1 or 2, the value of m being the same as the available valance of M.

3. A composition according to claim 2 wherein M is hydrogen or nickel.

4. A composition according to claim 2 wherein the stabilizing compound is O-mono(1,3,3-trimethyl-2-azabicyclo[2.2.2]octane-5-ol)sebacate.

5. A composition according to claim 2 wherein the stabilizing compound is nickel bis {o-mono(1,3,3-trimethyl-2-azabicyclo[2.2.2]octane-5-ol)sebacate].

6. A composition of claim 1 which contains additionally a stabilizing amount of a UV absorber.

7. A composition of claim 1 which contains additionally a stabilizing amount of a light stabilizer selected from the group consisting of 2(2-hydroxyphenyl) benzotriazoles, 2-hydroxybenzophenones, nickel complexes and benzoates.

8. A composition of claim 1 which contains additionally 0.01 to 2% of a thiosynergist having the formula

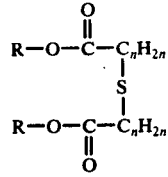

wherein R is an alkyl group having from 6 to 24 carbon atoms and n is an integer from 1 to 6.

9. A composition of claim 1 which contains additionally 0.005 to 5% of a phenolic antioxidant.

10. A composition of claim 1 which contains additionally
   a. 0.005 to 5% of a phenolic antioxidant and
   b. a stabilizing amount of a UV absorber.

11. A composition of claim 1 wherein the synthetic organic polymer is a polyolefin.

12. A composition of claim 11 wherein the polyolefin is polypropylene.

13. A composition of claim 11 which contains additionally 0.005 to 5% of a phenolic antioxidant selected from the group consisting of n-octadecyl 3-(3,5-di-t-butyl-4-hydroxyphenyl) propionate, di-n-octadecyl (3,5-di-butyl-4-hydroxybenzyl) phosphonate, pentaerythritol-tetrakis[3-(3,5-di-t-butyl-4-hydroxyphenyl)propionate], and tris-(3,5-di-t-butyl-4-hydroxybenzyl) isocyanurate.

14. A composition of claim 11 which contains additionally
   a. 0.005 to 5% of a phenolic antioxidant selected from the group consisting of n-octadecyl 3-3,5-di-t-butyl-4-hydroxyphenyl) propionate, di-n-octadecyl (3,5-di-t-butyl-4-hydroxybenzyl) phosphonate, pentaerylthritol-tetrakis[3-(3,5-t-butyl-4-hydroxyphenyl)propionate], and tris-3,5-di-t-butyl-4-hydroxybenzyl) isocyanurate, and
   b. A stabilizing amount of a UV absorber selected from the group consisting of 2(2'-hydroxy-3',5'-di-t-butylphenyl)-5-chlorobenzotriazole, 2-hydroxy-4-n-octoxybenzophenone, and 2(2'-hydroxy-5-methylphenyl)-benzotriazole.

* * * * *